(12) United States Patent
Hekmat et al.

(10) Patent No.: US 8,192,534 B2
(45) Date of Patent: Jun. 5, 2012

(54) OPEN LUMEN AIR FILTRATION FOR LIQUID LINES

(76) Inventors: Neema Hekmat, Mountain View, CA (US); Lipkong Yap, Singapore (SG)

( * ) Notice: Subject to any disclaimer, the term of this patent is extended or adjusted under 35 U.S.C. 154(b) by 292 days.

(21) Appl. No.: 12/681,142

(22) PCT Filed: Oct. 13, 2007

(86) PCT No.: PCT/US2007/021887
§ 371 (c)(1),
(2), (4) Date: Apr. 1, 2010

(87) PCT Pub. No.: WO2009/048452
PCT Pub. Date: Apr. 16, 2009

(65) Prior Publication Data
US 2010/0218679 A1    Sep. 2, 2010

(51) Int. Cl.
*B01D 53/22* (2006.01)
(52) U.S. Cl. ............ 96/6; 95/46; 95/241; 96/4; 96/155
(58) Field of Classification Search .......... 95/46, 241; 96/4, 6, 155
See application file for complete search history.

(56) References Cited

U.S. PATENT DOCUMENTS

| | | | | |
|---|---|---|---|---|
| 1,964,391 A * | 6/1934 | Thomas | ............ | 62/110 |
| 3,631,654 A * | 1/1972 | Riely et al. | ............ | 96/6 |
| 3,751,879 A * | 8/1973 | Allington | ............ | 96/5 |
| 3,844,283 A | 10/1974 | Dabney | | |
| 3,982,534 A | 9/1976 | Buckman | | |
| 4,227,527 A | 10/1980 | De Frank et al. | | |
| 4,276,170 A * | 6/1981 | Vaillancourt | ............ | 210/436 |
| 4,324,239 A | 4/1982 | Gordon et al. | | |
| 4,484,936 A * | 11/1984 | Sakai | ............ | 96/219 |
| 4,516,984 A * | 5/1985 | Warner et al. | ............ | 95/46 |
| 4,689,047 A | 8/1987 | Bauer | | |
| 4,985,055 A * | 1/1991 | Thorne et al. | ............ | 96/6 |
| 5,104,810 A * | 4/1992 | Birbara et al. | ............ | 436/161 |
| 5,106,754 A * | 4/1992 | Steele et al. | ............ | 436/146 |
| 5,108,367 A | 4/1992 | Epstein et al. | | |
| 5,334,153 A | 8/1994 | McIntyre et al. | | |
| 5,533,512 A | 7/1996 | Novotny et al. | | |
| 5,695,545 A * | 12/1997 | Cho et al. | ............ | 95/46 |
| 5,936,649 A * | 8/1999 | Ikeda et al. | ............ | 347/87 |
| 6,494,938 B2 * | 12/2002 | Sims et al. | ............ | 96/6 |
| 7,097,690 B2 * | 8/2006 | Usher et al. | ............ | 95/46 |
| 2001/0009126 A1 * | 7/2001 | Nagai | ............ | 96/6 |
| 2002/0022848 A1 | 2/2002 | Garrison et al. | | |
| 2004/0079692 A1 * | 4/2004 | Cote et al. | ............ | 210/220 |
| 2007/0089489 A1 * | 4/2007 | Lewnard et al. | ............ | 73/38 |
| 2007/0256561 A1 * | 11/2007 | Ooya | ............ | 96/6 |

* cited by examiner

*Primary Examiner* — Jason M Greene
*Assistant Examiner* — Anthony Shumate
(74) *Attorney, Agent, or Firm* — Adam Bell; Matthew Kaser (57) ABSTRACT

Devices and systems for capturing and removing accumulated gas bubbles in a liquid-carrying line wherein the device is an expanded double-layered chamber designed and adapted to be integrally placed within the flow pathway of a liquid-carrying line. The device allows insertion of tubes and wires through the device while in use without occlusion of the fluid flow path and without interruption of the bubble-removing function. The efficiency of the air venting and bubble-removing process is not dependent on the fluid flow rate under stable flow conditions, and the device works to remove air bubbles under a range of orientations.

19 Claims, 6 Drawing Sheets

Longitudinal Section of Air Filter with zero internal gauge pressure. In the coordinate displays, "R" and "Z" represent radial and axial, respectively.

Figure 1: Longitudinal Section of Air Filter with zero internal gauge pressure. In the coordinate displays, "R" and "Z" represent radial and axial, respectively.

Figure 2: Longitudinal Section of Air Filter with positive internal gauge pressure Figure 3: Cropped scaled view of microporous hydrophobic membrane under zero membrane hoop stress or zero fluid gauge pressure.

Figure 4: Cropped scaled view of microporous hydrophobic membrane under compressive membrane hoop stress or negative fluid gauge pressure.

Figure 5: Cropped scaled view of microporous hydrophobic membrane under tensile membrane hoop stress or positive fluid gauge pressure.

Figure 6: Longitudinal section of joint assembly detail

Figure 7: Diagram depicting position stability of air bubble at the top of the filter lumen with imposed blunt fluid and buoyancy forces to allow for venting of air through the hydrophobic membrane and outer casing.

Figure 8: Diagram depicting opening of check-valve when pressure inside filter is positive relative to its exterior.

Figure 9: Diagram depicting closing of check-valve when pressure inside filter is zero or negative relative to its exterior.

Figure 10: Graph of volumetric flow rate through porous 0.2 micrometer pore PTFE membrane Figure 11: Graph of volumetric flow rate through porous 1.0 micrometer pore PTFE membrane.

Figure 12: Graph of water intrusion pressures through PTFE membrane

Air ventilation performance with 100% air infusion through filter device

| trial | volume air unfiltered (cc) | volume air filtered (cc) |
|---|---|---|
| 1 | 1 | 9 |
| 2 | 2 | 8 |
| 3 | 3 | 7 |
| 4 | 2 | 8 |
| 5 | 1 | 9 |
| 6 | 3 | 7 |
| 7 | 2 | 8 |
| 8 | 2 | 8 |
| 9 | 2 | 8 |
| 10 | 2 | 8 |
| | mean ventilation: | 80.00% |
| | stdev ventilation: | 6.67% |

Figure 13: Table showing results of tests of prototype filter (results of testing of device prototype).

OPEN LUMEN AIR FILTRATION FOR LIQUID LINES

This application claims priority to PCT/US2007/021887.

BACKGROUND

The problem of gas bubbles in a fluid-carrying line is very a long-standing and well-known one. This problem is of considerable importance in various applications in which a liquid is conducted through a conduit, and is particularly troublesome in medical applications. Currently, there is no adequate solution to this problem. Gasses may enter the fluid-filled line in a gaseous state as bubbles within the fluid, or it may be present in a dissolved state within the fluid, and come out of solution under the influence of changing pressures or temperatures. The gas molecules so produced coaless under entropic and hydrophobic influences to form discrete bubbles within the fluid. These bubbles can interrupt and/or block the flow of a fluid. Such blockage or interruption can be problematic for many sorts of medical and industrial equipment where an uninterrupted flow is desirable. Many analytical and diagnostic devices, especially those that employ the flow of very small volumes of a liquid, are very sensitive to such interruptions in flow. When small volumes are involved or at low Reynolds numbers where viscous forces are dominant, the effects of surface tension and other forces at a liquid-gas phase boundary become pronounced and can inhibit flow. These problems are particularly acute in microfluidic applications.

In a medical context, when intubation is required, for example with a catheter, drip or other conduit designed to introduce (or remove) liquid from the body of a subject, such blockage or interruption can have adverse consequences and can even be fatal, such as when an air bubble enters the blood stream. Air embolism (for example venous, pulmonary or cerebral) is a well-known and potentially fatal complication that can occur in patients with central venous catheters (CVCs) as a consequence of the entry of air into the vasculature upon removal of the catheter, and many articles exist describing various methods used to prevent formation of an embolus. Less risk is associated with the use of peripherally inserted central catheters (PICC), but the risk of embolization is still a serious one. Venous air embolism (VAE) occurs mostly during surgical procedures in which the operative site is 5 cm or higher above the right atrium or gas is forced under pressure into a body cavity and is often cited as a complication of neurosurgery, but it can also occur during procedures involving the head and neck, laparoscopic procedures, vaginal delivery and caesarean section, and spinal instrumentation procedures.

The current approach to this problem is to manually prime the fluid line, by flushing fluid through it, just prior to use to ensure removal of any air bubbles present. The operator such as the doctor, nurse or paramedic, visually checks the visually translucent line to determine of any bubbles are present, often tapping the line to dislodge bubbles, and then flushes the line with excess fluid to make sure that any bubbles present are flushed out and that no bubbles are visually present.

Commercial valves and air vents may be placed within the line to prevent gas build-up and so that bubbles that do form may be removed from the line. Valves are usually manually employed by raising the line at the site of the valve so that the bubbles rise to the valve and then opening the valve to flush out any bubbles present.

Commercially available gas/air venting devices are available, particularly for use with medical applications, which are able to vent gas/air from liquid lines without need for manual vents or valves. Examples include IV air filter devices, such as those supplied by Pall Corp and Qosina Corp, and cardiopulmonary bypass surgery blood air filters, such as the Dynamic Bubble Trap by DeWitt Group Int'l and EC Blood Filter® by Pall Corp. These devices use hydrophobic micro-porous membranes to vent gas captured within IV tubes. To allow for sufficient exposure of air pockets/particles with the microporous membranes, the filter divides entering flow into micro-channels. By decelerating the advection rate of the air pockets and increasing the surface area-to-volume ratio, these microchannels allow for air bubbles to have greater contact with the membranes for filtration to occur. However the use of use of these air venting filters is limited primarily by their split channel design, which does not allow for compatibility with catheters, sheaths and endovascular interventional devices that largely require simultaneous passage of liquid and catheters/wires. Other limitations of these current technologies include an inherent dependence on infusion rate (flow rate) to control filtration efficacy, i.e. at higher flow rates, gases pass through the micro-channels faster and carry less contact with hydrophobic vent membranes. Also, the current technologies suffer from undesirable mechanical resistance to flow due to the split channel design. The design of the current invention addresses these three limitations by offering full compatibility with guidewires, catheters and other endovascular devices concurrent with liquid infusion. Since the device separates air/gas from infusing liquid solution, air filtration efficacy is decoupled from infusion rate. In addition, the single, continuous lumen imposes minimal mechanical resistance on flow and infusion capacity.

The current solutions, for example manual flushing of lines of openable valves positioned within a line, present other inherent problems. One current deficit is that the process of recognizing the presence or gas bubbles in the line is visual and requires active checking. Another deficit is that the process of removal of gas bubbles is manual and subject to human error. A further deficit is that such methods cannot remove air bubbles that may arise subsequent to checking and insertion of the line, such as when gas comes out of solution due to the effects of increasing temperature and or decreasing pressure. Another deficit of the current solution is that the efficiency of removal of air bubbles is at least partially dependent upon having a reasonably low fluid flow rate through the line. The faster the fluid flows in the line, the more likely it is that any bubble trapped in the line will pass by any valve and will not therefore be removed. Many infusing solutions (such as radio-opaque contrast solutions) are infused at a relatively fast rate, and thus, the current air venting mechanisms are not a viable solution. None of the current solutions contains an air bubble capture system or bubble trap that removes gas bubbles from the flowing liquid irrespective of the rate of liquid flow through the tube. Additionally, the current solutions do not adequately address the removal of air bubbles arising from the connection or re-connection of fluid lines and insertion of catheters/wires into, for example, a guide/introducer sheath.

There is a long-felt need for air venting devices that trap gas bubbles, that remove gasses from a line irrespective of the rate of fluid flow and that function while allowing insertion of wires, tubes and other solid devices during liquid flow.

Additionally there is a need for such air-venting devices that vent gas bubbles in many medical, analytical, diagnostic and industrial applications, such as hot water heating systems, cardiopulmonary pumps, contrast solution power injectors, endoscopes, chromatography apparatuses, and microfluidic devices e.g., the Fluidigm devices such as those described in U.S. Pat. No. 7,118,910 "Microfluidic Device And Methods Of Using Same"; U.S. Pat. No. 6,752,922 "Microfluidic Chromatography"; and U.S. Pat. No. 6,951,632 "Microfluidic Devices For Introducing And Dispensing Fluids From Microfluidic Systems"; each of which is hereby fully incorporated by reference for all purposes to the extent allowed by law.

A number of references describe technology and devices relevant to the present invention and show some previous solutions to the present technological problems. But none of these references disclose or suggest the present invention. These references include the following.

U.S. Pat. No. 4,689,047 "Air Venting Winged Catheter Unit". This disclosure describes a winged catheter unit enabling the user to introduce intravenous fluids while permitting the technician to control air venting at the onset of the I.V. introduction and during change of I.V. bottles without removal of the catheter.

U.S. Pat. No. 4,227,527 "Sterile Air Vent" describes a sterile air vent which permits the passage of gas but is substantially impervious to microorganisms. The vent is suitable as a tip protector for the tip ends of medical fluid administration sets or the like and filtering is provided by a solid microporous plug.

U.S. Pat. No. 5,334,153 "Catheter Purge Apparatus and Method of Use" describes balloon catheters with an air purging feature.

U.S. Pat. No. 4,324,239 "Safety Valve for Preventing Air Embolism and Hemorrhage" describes a safety valve with an integrated piston.

U.S. Pat. No. 5,533,512 "Method and Apparatus for Detection of Venous Air Emboli" describes a respiratory gas monitoring system to detect emboli.

U.S. Pat. No. 3,982,534 "Intravenous Administration System" describes an intravenous administration system with three separate units for delivering fluids.

U.S. Pat. No. 5,108,367 "Pressure Responsive Multiple Input Infusion System" describes an infusion system for administering multiple fluids at individually programmable rates and volumes. The system has a priming mode that detects and removes air bubbles in the fluid line.

U.S. Pat. No. 3,844,283 "Apparatus for Aseptically Dispensing a Measured Volume of Liquid Apparatus" discloses a device for dispensing volumes of liquid with a conventional cut-off valve to eliminate the need for introducing contaminating environmental air.

US20020022848A1 "Method and Apparatus for Minimizing the Risk of Air Embolism when Performing a Procedure in a Patient's Thoracic Cavity" describes an apparatus for minimizing the risk of air embolism includes an instrument delivery device having a gas outlet for delivering gas into a patient's thoracic cavity.

The present invention provides a simple and effective solution to the long-standing and well-known problem of gas bubbles in fluid-carrying lines. This problem is of considerable importance in various many applications, particularly in medical applications.

DEFINITIONS

In the present disclosure, the following words are used is the following ways.

"Line" is used to mean any elongated tube made of any material that may be opaque or translucent and that in various embodiments is made of an inert of biocompatible material such as silicone plastics or similar materials.

"Liquid" means any liquid including biological fluids, saline etc.

"Bubble" refers to any quantity of a gas in a liquid, whether visible or not.

"Venting" is a verb that refers to the removal of a gas from an enclosed area, such as from a liquid-carrying tube.

"Air filter" means a device designed to capture and/or remove a gas from a liquid flowing through a line. The word "trap" or "air trap" may also be used to describe such a device.

Gauge (or gage) pressure is defined as the pressure within the filter (at the inner surface of the filter membrane) minus the pressure at the outer surface of the filter casing.

The phrase "integrally placed within a line", when referring to an air filter, simply means that the air filter is placed within the lateral axis of a line such that a liquid flowing through the line will flow through the air filter. The air filter may be removable from the line and may be removably coupled into the line, using, for example, leur-lock or snap-fit joints gasket joints or any suitable locking joint that provides a liquid-tight seal under normal working conditions. To say that a filter is placed "in-line" with a conduit or tube or flow pathway or fluid-carrying line is the same as saying that the filter is "integrally placed within a line", as above.

To say that the inner and outer wall is "partially in contact" with the outer wall means that the two walls are in less than complete contact with each other. The walls may be in contact to any degree from 1 to 99.9% of their surface areas, such as 10%, 25%, 50%, 75%, 90% or 95% in contact with each other.

The word "diameter" when used with respect to pores in a membrane, refers to the longest distance between the sides of the pores, so that in the case of a diamond shaped pore, the diameter is the longest distance between any two points on the perimeter of the pore.

BRIEF DESCRIPTION OF THE INVENTION

The present invention encompasses devices, systems, methods and kits for removing accumulated gas bubbles in a liquid-carrying line. In various specific embodiments, the invention comprises the following.

A filter for capturing and removing accumulated gas bubbles present in a liquid-carrying line, the filter adapted for integration into the liquid-carrying line, the filter having an expanded chamber having an inlet end and an outlet end, wherein the maximum diameter of the expanded chamber is greater than the diameter of the portion of liquid-carrying line into which it is adapted to be integrated, and wherein the expanded chamber includes an inner wall and an outer wall constructed so as to form two concentric chambers having a liquid flow path through the axis of the inner chamber, and wherein the inner wall is, under conditions of use, permeable to gasses but impermeable to liquids.

The expanded chamber can be spherical or ovoid. The shape of the expanded chamber is asymmetrical, having a generally narrower diameter close to the inlet end and a generally broader diameter close to the outlet end.

The design of the present invention allows gas capture and venting while concurrently using instruments passing through the conduit, such as catheters, sheaths and endovascular interventional devices.

The design of the present invention allows for inserted cylindrical objects (e.g. wires, tubes) to be self-guided towards the outlet.

The axisymmetric design provides air filtering under all orientations, with optimal filtration performance under all flat rotational orientations. The device provides>80% filtration performance under low Reynolds numbers (less than ~10).

The design of the present invention means that filtration efficacy is generally not dependent on infusion rate (flow rate) under stable flow conditions. Our tests have shown stability in flow models simulating flows of up to 1200 cc/hr in a 8 Fr. compatible device (or Reynolds numbers of less than 4800). Unstable flow conditions occur when the Reynolds has reached the point where the fluid boundary layers are no longer separated by a core fluid stream and all fluid within the device is in a mixing regime.

The design of the present invention does not use a split channel design, but uses a single channel design, thereby reducing overall resistance to flow when compared with the split channel design. The single, continuous lumen imposes minimal mechanical resistance on flow and infusion capacity. In a split channel configuration, there is a split in a liquid line, in other words, a bifurcation or division of a central or inlet flow into two/more liquid channels. The split channel design filter has multiple (i.e. more than one) parallel-arranged paths for liquid flow. Therefore, in a split channel design filter liquid can take more than one fluid path from the device's inlet to its outlet. In the case of a medical filter employing this split channel design, the "split channels" are lined with a hydrophobic or other air-filtering membrane. The "split channels" are intended to increase the filtration surface area-to-air volume ratio to enhance filtration efficacy.

In contrast, in a non-split channel design filter, entering fluid can only take a single path from the inlet to the outlet of the device.

In various embodiments, the inner wall comprises a microporous membrane. In certain embodiments this microporous membrane is hydrophobic. The microporous membrane has pores that may have, for example, an average diameter of between 0.1-50 microns under zero hoop-stress. The microporous hydrophobic membrane may be comprised of a material selected from the group consisting of polytetrafluoroethylene, vinylidene fluoride (VDF), tetrafluoroethylene, vinylidene fluoride, hexafluoropropylene, carbon black, elemental sulfur, a glass composite, nylon, polyethersulfone and acrylic copolymer. In addition, to create a microporous membrane with hydrophobic properties, a material with minimal or void of hydrophobic properties, such as polyvinylidene difluoride (PVDF) or cellulose, may be used as a base substrate by coating it with a hydrophobic material (such as those presented above). In some embodiments, the microporous membrane has pores that are diamond shaped. The pores are designed to open or become more open when the membrane is stretched.

In various embodiments, the outer wall is made of a perforated material selected, for example, from the group of plastics consisting of acrylic, ABS [Acrylonitrile Butadiene Styrene], Methyl Methacrylate Acrylonitrile Butadiene Styrene, nitrile, polycarbonate, polyethylene, nylon, PVC [polyvinyl chloride], acetyl, silicone, polysulfone, polystyrene, polyisoprene, copolyester, polyethersulfone, polyvinylidene fluoride, polyurethane, ethylene vinyl acetate copolymer and polypropylene. This outer wall may also be made of a metallic material, such as stainless steel, copper, nickel-coated steel, brass, aluminum, silver, iron or nickel-titanium. The perforated material may be made of a translucent material, may be gas permeable or impermeable, and may have valves integrated within it. The outer wall may be flexible or rigid.

In use, when the internal pressure inside the inner wall increases, the inner wall expands to fill the volume in which it resides, contacting and pushing outwards upon the outer wall.

The filter acts passively and automatically to trap and air bubbles present in the liquid flowing through the line and is designed so that the microporous membrane becomes increasingly gas permeable with increasing liquid pressures within the liquid flow path.

DETAILED DESCRIPTION OF THE INVENTION

The invention provides devices, systems, methods and kits for removing accumulated gas bubbles in a liquid-carrying line.

Embodiments of the present invention encompass a device that filters, captures and vents gas bubbles from a liquid-carrying line. The filter of the invention maintains an open lumen to allow for insertion of tubes and wires (e.g. catheters and guidewires for endovascular intervention related applications) through the device concurrent with liquid infusion through the device.

Important advantages of the present design include the following: (1) The design of the present invention allows gas capture and venting while concurrently using instruments passing through the conduit, such as catheters, sheaths and endovascular interventional devices. (2) The design of the present invention means that filtration efficacy is not dependent on infusion rate (flow rate). (3) The design of the present invention does not use a split channel design, but uses a single channel design, thereby reducing overall resistance to flow when compared with the split channel design. The single, continuous lumen imposes minimal mechanical resistance on flow and infusion capacity.

In a general embodiment, the air filter comprises an expanded chamber designed and adapted to be integrally placed within a line, the expanded chamber having an inlet end and an outlet end. The diameter of the expanded chamber is greater than the diameter of the line into which it is integrated.

The shape of the expanded chamber, in certain embodiments, can be approximately spherical or ovoid. The expanded chamber can be of an asymmetrical shape that is narrower close to the inlet end and broader close to the outlet end. In other embodiments, the expanded chamber can be of other shapes such as rectangular, polyhedral or irregular.

In certain embodiments, the ratios of dimensions of the filter are as, for: [inlet flow diameter:max luminal diameter: total filter length], vary as follows: [1:5.5:28], [1:9.5:30 ], [1:9.5:54] (The filter dimension ratios may be any value between the three sets provided above). These values represent dimensionless units which are normalized over the inlet flow diameter and may be apply to any size structure proportionally within the ranges provided.

In certain embodiments, the expanded chamber is made of a plastic material that is rigid, and in other embodiments, can be made of a non-rigid, flexible and/or elastic material.

In some embodiments, the expanded chamber is translucent, allowing an operator to see within the chamber, to visually determine whether bubbles and/of liquids are present.

In a preferred embodiment, the expanded chamber is a double-walled chamber having a first, inner wall and a second, outer wall. Essentially the structure resembles an inner bag that is contiguous with the fluid flow path through the line, and an outer bag that surrounds the inner bag. In preferred embodiments, the first, inner wall comprises a microporous membrane. A microporous membrane is a thin-walled structure with a plurality of pores extending through the thickness of the material. A hydrophobic microporous membrane is a microporous membrane carrying resistance and strong aversion to wetting and penetration of water-based liquids/solutions.

In certain embodiments, the second, outer wall (also called outer casing) comprises a perforated, liquid-porous or gas-porous material, and in other embodiments the outer wall is not perforated and is impermeable to fluids but may have valves integrated within it.

The first and second walls may be in contact with each other or partially in contact with each other over some percentage of their areas, or may have an air gap between them and be substantially separated from one another. In certain embodiments, the microporous hydrophobic membrane of the inner wall is substantially in contact with perforated outer casing.

Figure 2:
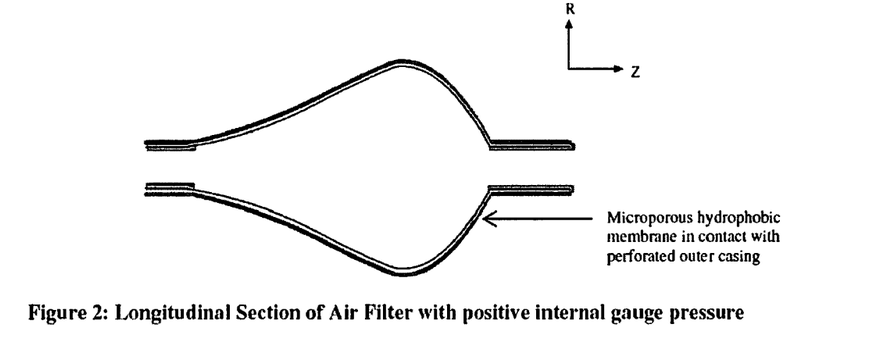
FIG. 2 is a schematic drawing that shows a longitudinal section of the air filter with positive internal gauge pressure.

In use, when the internal pressure inside the first (inner) wall increases, the first wall expands to fill the volume in which it resides, contacting and pushing outwards upon the second (outer) wall. See FIG. 2 that shows the air filter with positive internal gauge pressure.

The air filter is positioned within the lateral axis of a line such that a liquid flowing through the line will flow through the air filter.

In use, the air filter will be positioned in an approximately horizontal orientation with respect to the ground. The greater the expansion of the filter luminal profile relative to the inlet/outlet diameter, the higher the capacity to bring the filter to near a vertical position without risking migration of bubbles downstream. Buoyancy is only one kinematic driver of gas bubbles towards the membrane for ventilation. Two others are decelerating flow within the lumen and the high pressure gradient across the membrane observed by gas pockets (because of the membrane's hydrophobic properties this gradient is not "felt" by water). Under slower flow rates and large expanded shape, the majority of gas pockets would be vented by the filter if placed in a true vertical orientation. Due to these three drivers, the filter achieves optimal filtration when placed in a true horizontal position (perpendicular to the earth's gravitational axis). In a vertical position, buoyancy is working against the intended mechanism of the filter, however, the pressure gradient across the membrane and decelerating flow will allow for less than optimal filtration to take place. Under lower Reynolds conditions, where the pressure gradient and decelerating flow significantly overcome the antagonizing buoyancy forces, reasonable filtration efficacy may be achieved. In use, gasses and bubbles are trapped by and collect within the expanded chamber and do not simply pass through it as would happen in a vertical orientation. To say that the air filter is positioned in an approximately horizontal orientation with respect to the ground means that the long axis of the air filter forms an angle of not more than about 45 degrees to the horizontal.

In certain preferred embodiments the air filter has an axi-symmetric design, such that at any point along the axis of the filter a cross section would be a perfect circle. The implication of the axi-symmetric design is that the filter has equivalent performance under all rotational orientations. The air filter has a diffuser-shaped entrance and nozzle-shaped exit, where the two shapes are merged in a parabolic configuration. The goal of the filter profile is to decelerate flow without creating unstable flow separation zones. Upon entering the inlet of the filter, the flow decelerates due to an expansion of the filter lumen (expansion may be of a straight/linear or curved shape). At the mid-section of the filter (marked by termination of the diffuser and the section with the largest inner diameter), the flow reaches its lowest velocity within the filter. Towards the distal end of the filter, the filter must restore flow to its original velocity, which is achieved by a nozzle shaped distal end (this nozzle also may be of linear/straight or curved shape. However, the transitions between the diffuser, expanded section of the filter and nozzle must be smooth to ensure optimal flow stability within the filter. Instability would cause mixing of gas and water within the filter and not allow for gas to maintain a steady position for ventilation. Thus the filter provides a parabolic transition between the diffuser and nozzle sections of the filter. However, more generally this transitional shape must be smooth (i.e. no notches, grooves, edges, etc). Another purpose for the nozzle end of the filter is to provide a means for a cylindrical-shaped object (e.g. wire, tube) which is inserted through the filter to self-guide itself towards the outlet.

Figure 1:
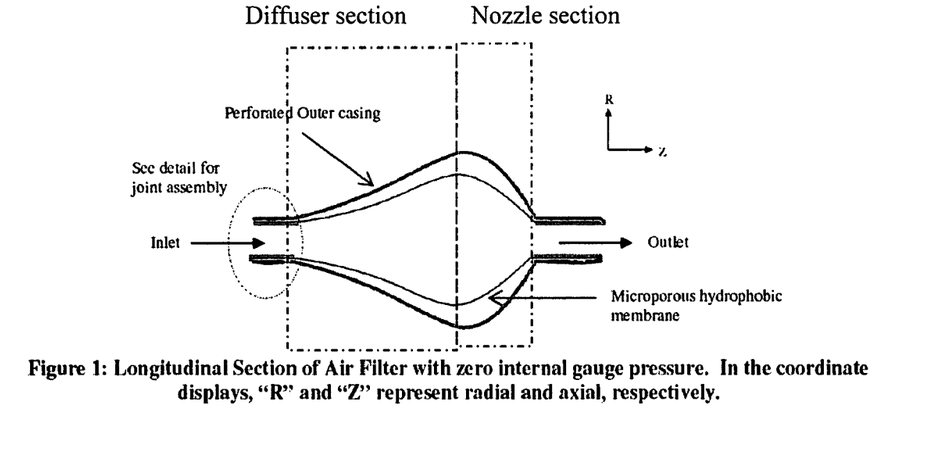
FIG. 1 is a schematic drawing showing a longitudinal section of the air filter with zero internal gauge pressure. In the coordinate displays, "R" and "Z" represent radial and axial, respectively.

In a preferred embodiment, the filter is composed of at least two different materials (see FIG. 1). The inner wall consists of a microporous hydrophobic membrane which serves as an obstruction to liquid but not air. The material of this microporous membrane may, for example, be PTFE (polytetrafluoroethylene), a glass composite, nylon, polyethersulfone or acrylic copolymer or other similar materials.

In preferred embodiments, the pore sizes of the microporous hydrophobic membrane are sufficiently small under zero hoop-stress so that when the internal fluid pressure in the line falls below that of ambient pressure (the pressure on the outside of the filter device), the small-sized pores present high resistance to air flow at zero and negative gage pressures. Under positive pressures within the filter, the membrane will stretch and cause the pores to open. The size of the outer casing acts as a maximum limit for the stretching and opening of the membrane pores, which by design, prevents over-stretching of the pores and an otherwise unacceptable water breakthrough pressure capacity. Under negative and zero gauge pressures within the filter, the pores remain "shut" (similar to a valve mechanism), thus preventing air/gas from entering the filter lumen.

The average pore sizes of the microporous hydrophobic membrane may range from between 0.2-20 microns in diameter under zero hoop-stress (i.e. stress in the circumferential direction). The average pore diameter under zero hoop-stress may, for example, range from 0.01 to 200 microns; from 0.05 to 150 microns; from 0.1 to 100 microns; from 0.1 to 50 microns; from 0.2 to 50 microns; from 0.2 to 20 microns; from 0.5 to 10 microns; from 0.05 to 20 microns; or from 0.5 to 10 microns.

The pores of the microporous hydrophobic membrane will be further collapsed by compressive hoop stresses. Compressive hoop stresses occur under negative gauge pressures within the filter. Closing of the pores under negative pressure prevents gas from intruding into the filter lumen. For example, when the filter is applied to a catheter device, if blood is drawn through the catheter (e.g. via a syringe), negative pressure will develop within the filter, closing the pores to act like valves to inhibit gas flow into the filter.

The pore size and pore density of the membrane is such to allow for a sufficient rate of passage of air across the filter membrane under anticipated pressure gradient ranges (where pore diameter ranges from 0.2-20 microns and pore density is between 10-50%). Sufficiency of rate of air flow across the membrane is based on desired volumetric gas filtration rate. In selecting the optimal membrane, considerations may include anticipated internal pressures within the filter and the maximum flow/infusion rate through the filter. The achievable gas volumetric flow rate through the filter is governed by pore density (relative amount of open area for gas to penetrate membrane) and internal filter pressure (i.e. pressure gradient to drive flow through membrane). The water break-through pressure is dictated by the membrane's pore size (i.e. pressure at which the water's pressure gradient across the membrane exceeds the hydrophobic interfacial tension). Thus, this membrane's pore size is selected such that under the range of anticipated filter pressures, the membrane does not exceed its breakthrough pressure. Thus the filter of choice may be the one which has the opportunity to vent a 100% gaseous infusion through the filter.] Any pressure above zero psi may allow gas to flow out of the filter. Pressures at or below 0 psig will not allow passage of gas in/out of the filter.

The thickness of the microporous hydrophobic membrane is relatively small, ranging from between about 0.0127 mm-1.27 mm. A thinner membrane is more easily 'stretchable' than a thick membrane. Under a given gauge pressure, a thinner membrane will stretch more due to higher hoop stress than a thicker membrane. Higher gauge pressure within the filter is caused by higher infusion rate through the filter. In medical applications, if a catheter or sheath is placed within blood, the filter is by default subjected to blood pressure. Infusion through the catheter/sheath would further drive the pressure within the filter. Thus, under higher flow rates, opening of the pores will facilitate higher gas filtration capacity and allow for the filter to better meet the increased demand for gas ventilation. The ability for decreased air resistance through the membrane under higher liquid pressures allows for a higher rate of passage of air through the membrane during higher liquid flow rate conditions. Therefore the air bubble filtration capacity of the device automatically adjusts with flow liquid rate and a greater volume rate of air bubbles may be captured and removed when most needed.

The outer wall consists of a stiff, densely-perforated (between 30-80% porosity) outer casing constructed using materials such as acrylates, ABS, polycarbonate, polyethylene, nylon, PVC or polypropylene, which protects the inner membrane from physical damage, permits transmission of venting air (with minimal imposed resistance to air flow) and prevents overstraining of the inner membrane during high pressure flow. Porosity is defined by the ratio: (total open area on a surface)/(total closed and open surface area). The inner hydrophobic membrane is sized to be smaller than that of the outer casing under neutral pressure (see FIG. 1). This enables the membrane to stretch when fluid (see FIG. 2) pressures are higher than that of ambient, thus causing the pores to open and decrease their resistance to air flow when fluid is entering the inlet of the filter.

Figure 3:
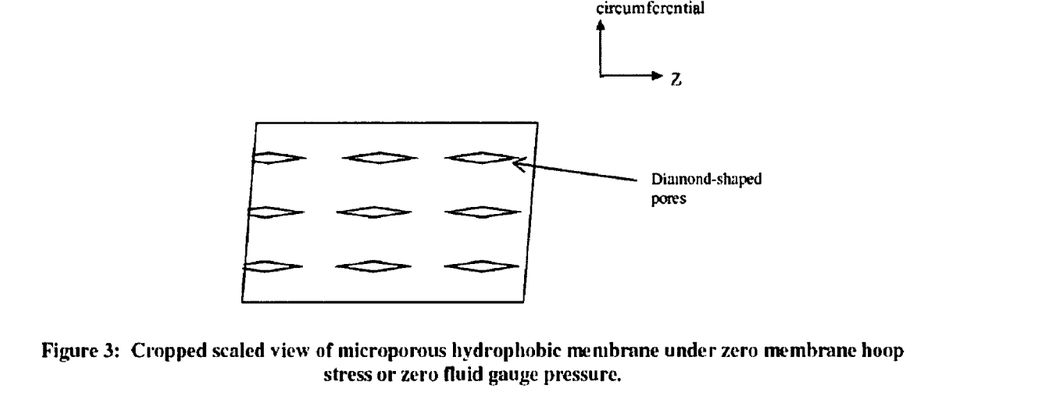
FIG. 3 is a schematic drawing of a magnified view of the microporous hydrophobic membrane under zero membrane hoop stress or zero fluid gauge pressure.
Figure 4:
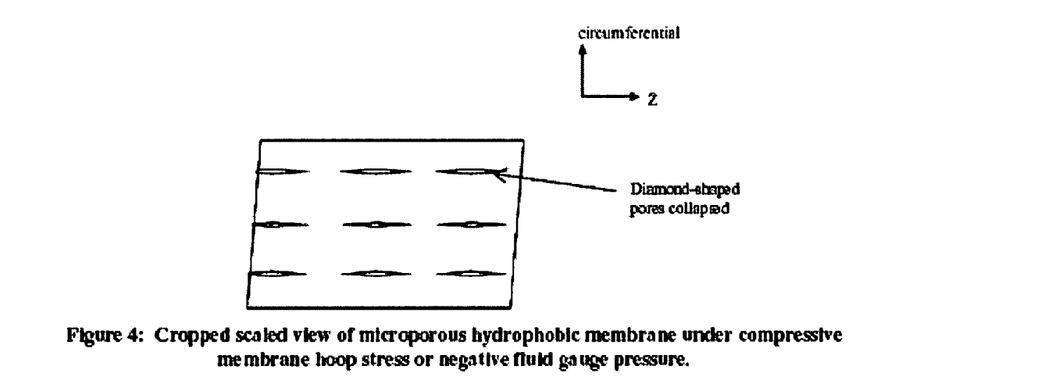
FIG. 4 is a schematic drawing of a magnified view of the microporous hydrophobic membrane under compressive membrane hoop stress or negative fluid gauge pressure.
Figure 5:
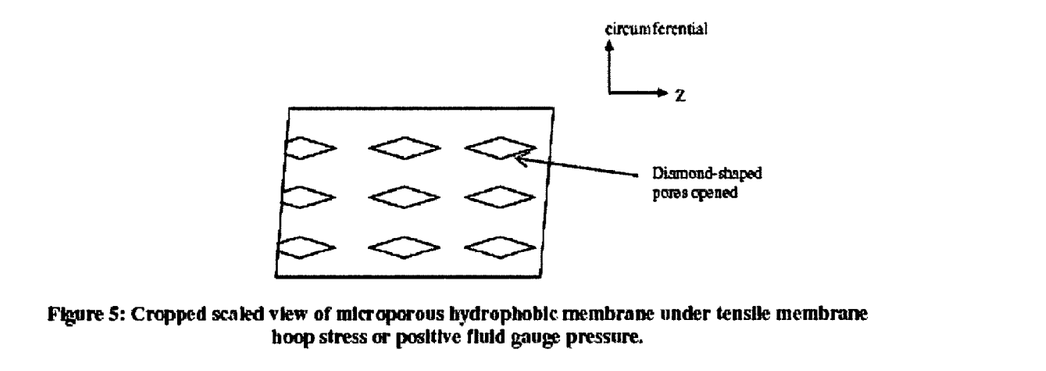
FIG. 5 is a schematic of a magnified view of the microporous hydrophobic membrane under tensile membrane hoop stress or positive fluid gauge pressure.

The pores of this membrane may be diamond shaped, where their long axes are oriented in the axial direction of the filter (axial direction is the principal direction of the fluid stream) (See FIG. 3). This shape facilitates stress concentration points at the corners of the diamond pores, thus causing for more pronounced collapse of the pores under negative gauge fluid pressures. (negative gauge pressures are those where the pressure within the filter is below that external/outside of the filter), or under compressive membrane hoop stresses) to further decrease permeability to air (see FIG. 4). Likewise, the shape allows for more pronounced opening of the pores under positive gauge fluid pressures (or tensile membrane hoop stresses) to further ease the resistance to air flow through the membrane (see FIG. 5).

In another embodiment, the filter is comprised of three components: (1) a microporous hydrophobic membrane, (2) a stiff, solid outer casing, and (3) one or more valves.

The microporous hydrophobic membrane forms the inner layer of the filter and serves as an obstruction to liquid but not to air. The pore size and density of the membrane are such to allow for sufficient rate transport of air volume across the filter membrane under anticipated pressure gradient ranges. A thicker membrane may be employed, than that described for the first variation (where thickness ranges between 0.050" to 0.200"), to allow for a more shape-stable membrane contour and greater consistency in flow patterns under varying fluid pressures.

With a thicker membrane, larger and/or greater density pore configurations (pore sizes ranging between 20-200 microns and 50-90% pore density) may be utilized to maintain the desired air filtration capacity.

The second element is the stiff, solid outer casing that protects the inner membrane from physical damage. This casing prevents over-straining of the inner membrane during cases of high pressure flow.

The third element comprises one or more check-valves (one-way valves) that are incorporated into an un-perforated outer casing that is impermeable to both gases and liquids. The valve(s) is/are aligned to permit fluids (gasses and liquids) from flowing from inside to outside the casing when the interior pressure is greater than exterior pressure. These valves permit exiting of gas that enters the space between the membrane and the outer casing, which has been originally vented from within the inner membrane]. The valve is closed when the external pressure exceeds or equals the internal pressure.

Figure 8:
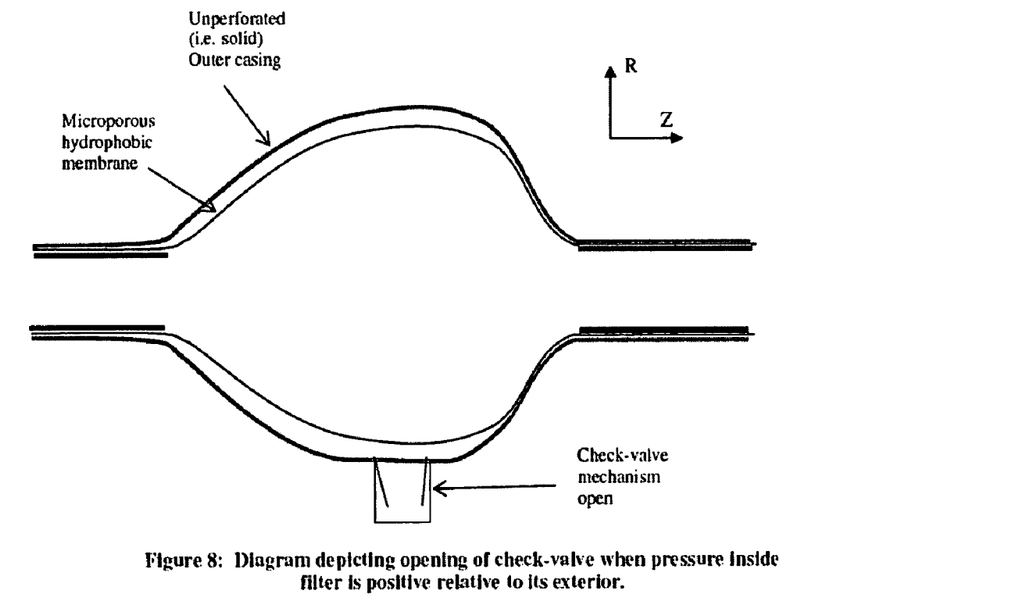
FIG. 8 is a schematic diagram depicting the opening of a check-valve when pressure inside the filter is positive relative to its exterior.
Figure 9:
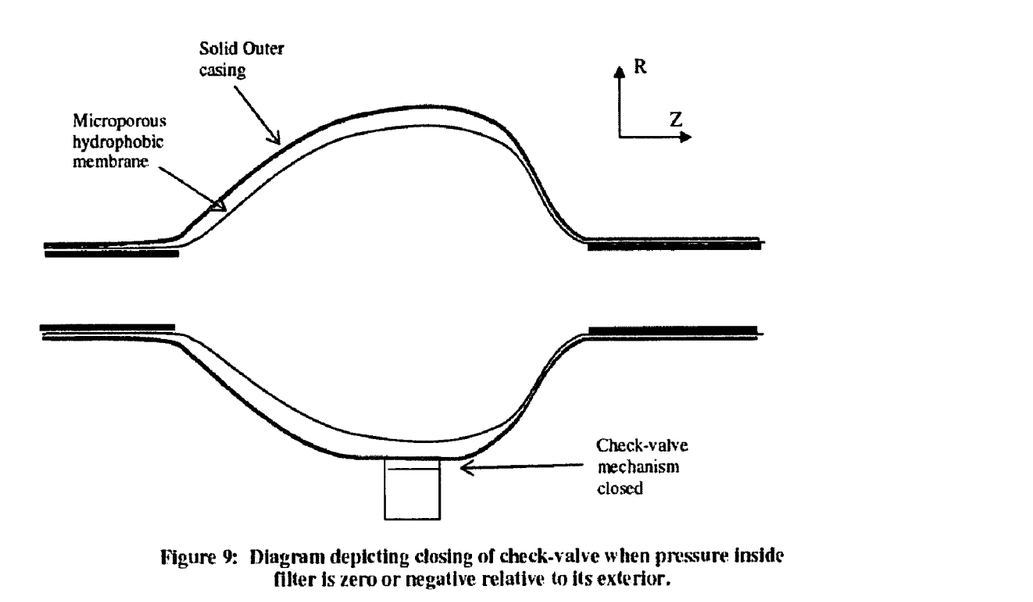
FIG. 9 is a schematic diagram depicting the closing of a check-valve when pressure inside filter is zero or negative relative to its exterior.
Figure 10:
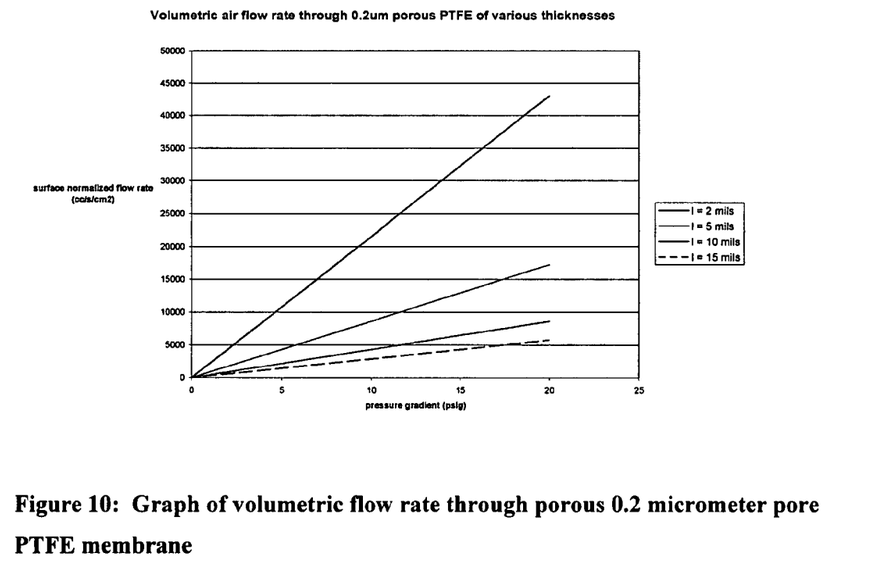
FIG. 10 is a graph of volumetric flow rate through porous 0.2 micrometer pore PTFE membrane
Figure 11:
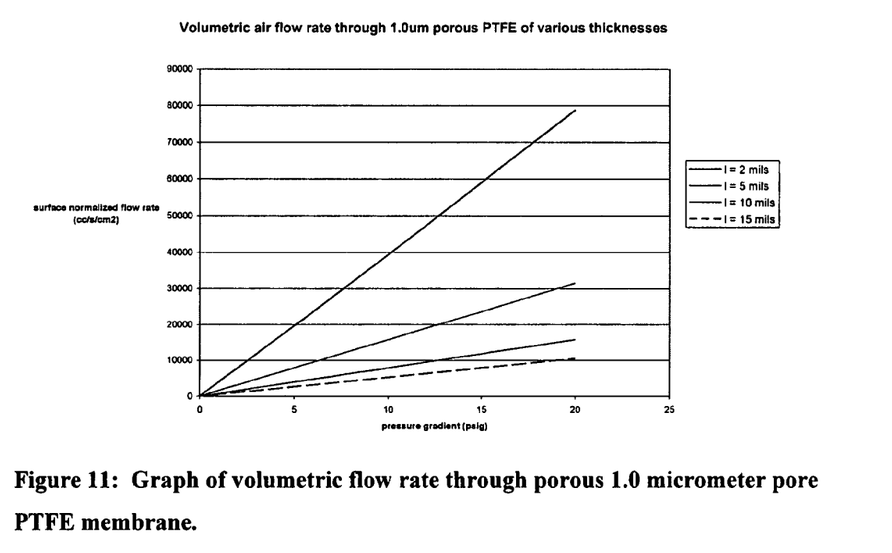
FIG. 11 is a graph of volumetric flow rate through porous 1.0 micrometer pore PTFE membrane
Figure 12:
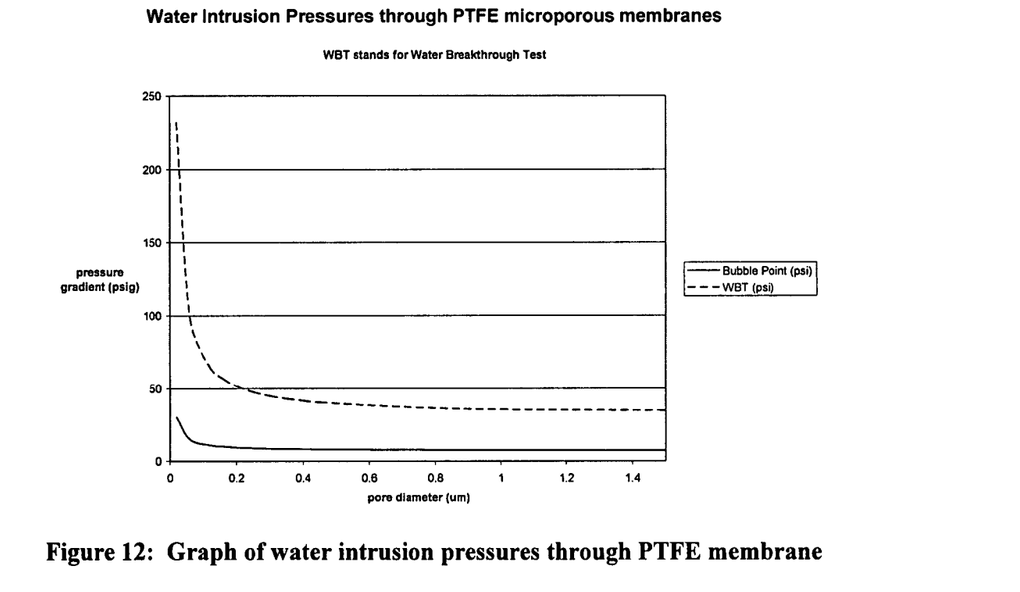
FIG. 12: is a graph of water intrusion pressures through PTFE membrane
Figure 13:
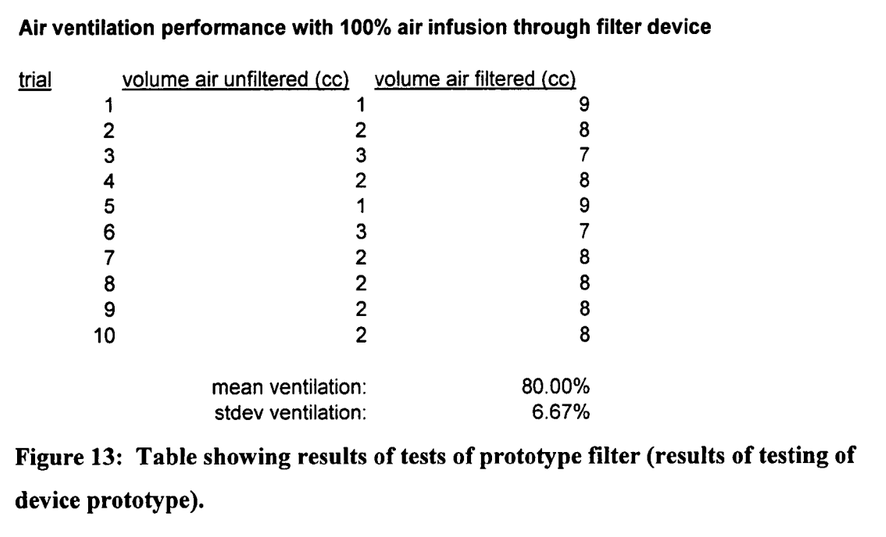
FIG. 13: is a table showing results of tests of prototype filter

When air flows from the internal fluid medium and through the porous inner membrane, the resulting pressure created between the outer casing and inner membrane activates opening of the valve and venting of air from the outer casing (see FIG. 8). Under such conditions, where the inner fluid pressure may drop below that external (e.g. negative internal gage pressure), the valve shall close to prevent ambient air from entering through the outer casing and inner membrane (see FIG. 9). In the case of selection of a thin porous membrane (as described above), the inner hydrophobic membrane may be sized smaller than that of the outer casing under neutral pressure (see FIG. 1) to provide a means for modulation of the air venting rate based on the volumetric flow rate through the filter.

In addition to the pore shapes described above, the pores may be round or oval in shape.

Figure 6:
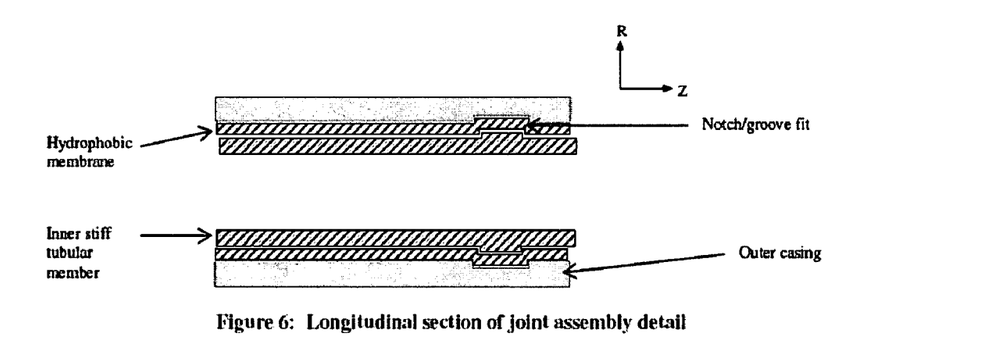
FIG. 6 is a drawing showing a longitudinal section of the joint assembly in detail.

The hydrophobic membrane is joined at the inlet and outlet ends of the filter to the outer casing by means of a compression fit between the outer casing and an inner stiff tubular member, i.e. the outer diameter of the inner stiff tubular member may be the same or slightly larger than that of the outer casing at its inlet and outlet ends (see FIG. 6). The outer casing may include a circumferential groove and the inner stiff tubular member a matching notch to facilitate a stronger joint between the three said members. A gasket of ring clamp may also be employed to provide a seal. An adhesive may also be applied within the inner layers of the compression fit to further improve the strength of the joint.

Figure 7:
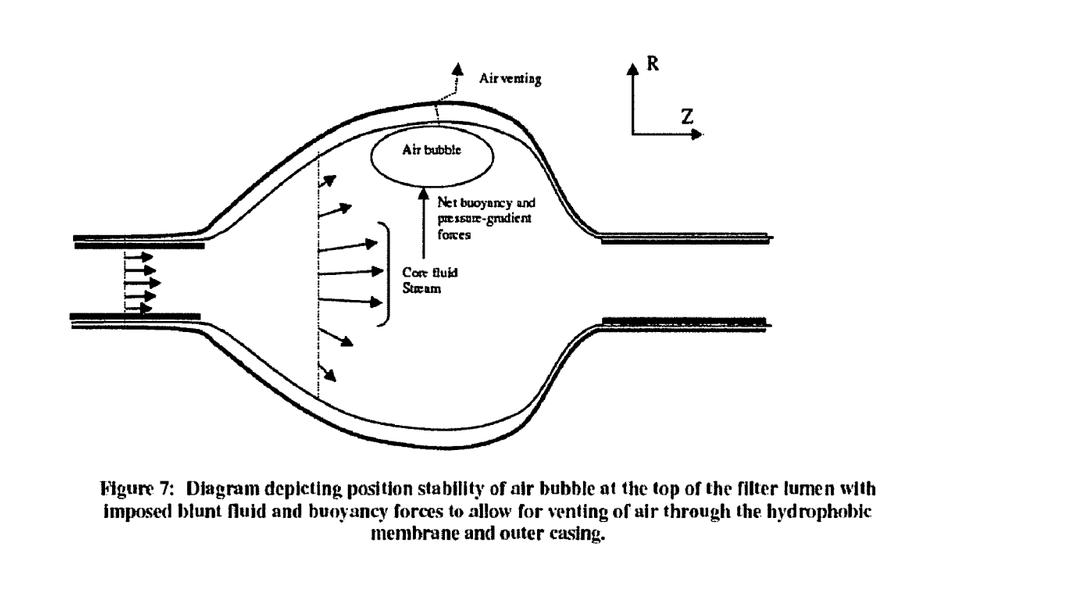
FIG. 7 is a schematic diagram depicting position stability of air bubble at the top of the filter lumen with imposed blunt fluid and buoyancy forces to allow for venting of air through the hydrophobic membrane and outer casing.

The gradual expansion of the filter diameter allows entering fluid to maintain minimal flow separation relative to the inner surface, while causing a net decrease in the mean flow velocity within the expanded section. In orientations where the filter is placed such that its axial axis is near perpendicular to that of gravity, entering air/gas bubbles are pulled upward by resulting buoyancy forces and pressure gradients (see FIG. 7) across the hydrophobic membrane induced. When the axis of the filter is oriented approximately perpendicular to the axis of gravity, buoyancy is a driver for gas bubbles to "rise" towards the inner surface of the membrane. The pressure gradient drives the penetration of air/gas bubbles across the membrane. This pressure gradient exists independent of the orientation/position of the filter relative to gravity.

The design of the filter is such that under reasonable volumetric flow rates, the advection speed of air bubbles in a decelerated flow within the filter is sufficiently slow that the buoyancy and pressure-gradient forces on the air bubble are able to carry it to the top of the filter. Once at the top of the filter, the bubble experiences decreased drag by the blunt flow, as it has moved away from the main section of the fluid stream. By means of the imposed buoyancy, pressure gradient forces and the physical obstruction presented by the nozzle end of the filter, the air bubble is held in a stable position for venting through the hydrophobic membrane. Buoyancy and pressure gradients act to drive gas bubbles towards the membrane, which is in a direction perpendicular to the infusing flow. The acceleration and speed of the gas bubbles in the 'vertical' direction (i.e. perpendicular to the filter axis) must be sufficiently larger than the 'horizontal' speed of the bubbles so that the final termination of the trajectory of the bubbles is at the membrane. For example, in shorter length filters, where the 'horizontal' speed of the air bubbles may be high, the buoyancy and pressure gradients would have to be large to ensure that the gas bubbles have opportunity to make contact with the filter membrane for ventilation. In "blunt flow" the gas bubbles in contact with the membrane can be considered as a blunt object relative to liquid flow, which is imposing a drag on the bubbles. Thus the buoyancy is acting as a kinematic force on the bubble.

To allow for flow stability and sufficiently decelerated flow within the filter lumen, under worst-case high rate or turbulent flow conditions in the inlet fluid line (where Reynolds number exceeds 60,000), the length of the filter (from the start of the diffuser to the end of the nozzle) must be at minimum of 8 times the difference between its largest diameter and the entering fluid line diameter. In various embodiments the length of the filter may be 8, 9, 10, 12, 15 or 20 times the difference between its largest diameter and the entering fluid line diameter.

The filter can be described as being constructed of a nozzle part (See FIG. 1) and a diffuser part (See FIG. 1). The nozzle and diffuser parts are joined together at a position between the center of the filter and about $3/5^{th}$ to $9/10^{ths}$ of the way along the total length of the filter (where measurement is taken from the inlet point of the filter) of the filter axis.

The filter is designed to be easily fitted or retro-fitted into an existing line simply by cutting the line and inserting the filter by means of fluid-tight joints in the in-flow and out-flow sides. Standard, commercially available tube fittings may be employed to integrate the filter into a line. The filter is designed to work with any type of fluid to remove any type of gas bubbles.

In one exemplary embodiment the fluid is a biological fluid such as saline, blood, plasma, or any therapeutic solution, and the fluid carrying line is an intravenous (IV) tube that carries liquids from a reservoir to a patient.

In another embodiment, the filter may be used in a microfluidic device for performing polymerase chain reaction, chromatography, sequencing, chemical or physical analysis, or for growing crystals for crystallography applications such as the devices described in US application Nos. 20020117517, 20050201901, 20060000513, and 20070138076.

Another embodiment and application of the present invention would be the use of the filter in printers that dispense liquid ink, such as ink-jet printers. Uninterrupted and consistent ink flow is critical in such applications and bubbles that block ink flow, for example in the print head, are very problematical. The current filter addresses this problem by removing air bubbles from the liquid ink as it flows through a dispensing line.

OBJECTS AND ADVANTAGES OF THE INVENTION

The invention provides an air filter capable of capturing and drawing air bubbles away from the main section of a fluid stream by means of buoyancy, air-specific pressure gradients and decelerating flow towards a hydrophobic membrane for venting of the bubble out of the fluid line. The filter stores captured air bubbles in a fixed position away from the central core of the fluid stream, such that, under an anticipated range of volumetric flow rates, the venting process is decoupled from the rate of fluid entering the filter.

The filter may be constructed of a hydrophobic membrane of slow air venting properties but carrying a high water-intrusion pressure threshold. Due to the fact that the cross-sectional profile of the filter is large relative to the connecting fluid lines at the inlet and outlet ends, the filter provides a highly energy efficient passive component, as it presents little mechanical resistance to passing flow and therefore has little effect on fluid pressure. As the filter maintains an open, non-constricting or obstructed lumen from its inlet to outlet, the filter can be used in fluid lines, where solid objects, such as wires and tubes may be passed through. The axi-symmetric shape of the air filter allows it to function in the same fashion regardless of its circumferential orientation. Furthermore, the filter contour shape provides a degree of flexibility as to how the axial axis of the filter is placed relative to that of gravity, while maintaining the intended functionality of the air filter.

The present invention provides the following advantages, amongst others.
1) It efficiently removes gas bubbles from a liquid-carrying line.
2) It functions automatically with no active observation or manual operation required.
3) It is easy to use and simple to maintain.
4) It is simple an inexpensive to manufacture.
5) The invention functions without the need for power input.
6) It captures and removes gas bubbles regardless of the flow rate of the fluid in the line. This has been demonstrated up to Re=4800, which incorporates the workable & severe range of infusion rates within medical applications.
7) The invention allows insertion of devices such as tubes and wires (catheters etc) through the device while in use without occlusion of the fluid flow path and without inhibition of its bubble-trapping function.
8) The efficiency of the air venting and bubble-removing process is independent of the fluid flow rate over a large range of Reynolds conditions. The system has been experimentally validated up to Re.=4800.
9) The device works to remove air bubbles in a wide range of orientations from horizontal to vertical.
10) The device prevents intrusion of air during zero or negative gauge pressure conditions. 10) The low resistance design does not constrain or impede fluid flow.
11) The present invention does not use a split channel design, but uses a single channel design, thereby reducing overall resistance to flow when compared with the split channel design and allowing for insertion of wires and tubes.

Other Embodiments of the Invention

In addition to the embodiments described above, other embodiments of devices, systems, methods and kits for removing accumulated gas bubbles in a liquid-carrying line are encompassed by the present invention. The invention encompasses various equivalent embodiments that employ materials and components that may differ from but be functionally equivalent to the invention explicitly described.

The present invention may be employed in embodiments related to any system in which a liquid is flowed within a line, such as in industrial processing and manufacturing systems, and analytical and diagnostic systems and in microfluidic systems, which are particularly susceptible to interruption in fluid flow due to gas bubbles. In various exemplary embodiments the air filter of the invention is fitted within a fluid delivery line of a spectrometer, a sample dispenser or a microfluidic device dispensing volumes on liquid in the microliter or nanoliter volumes. The invention also encompasses a method of using the air filters described by providing the air filter and placing it within a fluid flow path within a liquid-carrying line. The invention also encompasses systems comprised of a device such as, for example, a spectrometer, sample dispenser a microfluidic device and an air filter as described. The invention further encompasses kits for fluid manipulation that comprise at least a line adapted to contain a liquid and at least one air filter of the invention.

General Representations Concerning the Disclosure

The embodiments disclosed in this document are illustrative and exemplary and are not meant to limit the invention. Other embodiments can be utilized and structural changes can be made without departing from the scope of the claims of the present invention. As used herein and in the appended claims, the singular forms "a", "an", and "the" include plural reference unless the context clearly dictates otherwise. Thus, for example, a reference to "a part" includes a plurality of such parts, and so forth.

In the present disclosure reference is made to particular features of the invention. It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally.

The embodiments disclosed in this document are illustrative and exemplary and are not meant to limit the invention. Other embodiments can be utilized and structural changes can be made without departing from the scope of the claims of the present invention. In the present disclosure, reference is made to particular features (including for example components, ingredients, elements, devices, apparatus, systems, groups, ranges, method steps, test results, etc). It is to be understood that the disclosure of the invention in this specification includes all possible combinations of such particular features.

As used herein and in the appended claims, the singular forms "a", "an", and "the" include plural reference unless the context clearly dictates otherwise. Thus, for example, a reference to "a part" includes a plurality of such parts, and so forth.

The term "comprises" and grammatical equivalents thereof are used herein to mean that, in addition to the features specifically identified, other features are optionally present. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number.

Where reference is made herein to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). The numbers given herein should be construed with the latitude appropriate to their context and expression; for example, each number is subject to variation which depends on the accuracy with which it can be measured by methods conventionally used by those skilled in the art.

This specification incorporates by reference all documents referred to herein and all documents filed concurrently with this specification or filed previously in connection with this application, including but not limited to such documents which are open to public inspection with this specification.

The invention claimed is:

1. A filter for capturing and removing accumulated gas bubbles present in a liquid-carrying line, the filter adapted for integration into the liquid-carrying line, the filter comprising an expanded chamber having an inlet end and an outlet end, wherein the maximum diameter of the expanded chamber is greater than the diameter of the portion of liquid-carrying line into which it is adapted to be integrated, and wherein the expanded chamber comprises a single inner wall and an outer wall constructed so as to form two concentric chambers having a liquid flow path through the axis of the inner chamber, and wherein the inner wall is, under conditions of use, permeable to gasses but impermeable to liquids wherein the shape of the expanded chamber is spherical or ovoid and wherein the shape of the expanded chamber is asymmetrical, having a generally narrower diameter close to the inlet end and a generally broader diameter close to the outlet end such that in use, air bubbles present in the liquid carrying line are held in a stable position for venting through the inner wall.

2. The filter of claim 1 wherein the expanded chamber has a single inner wall and a single outer wall separated by a gap constructed so as to form two concentric chambers and a single channel through which liquid passes.

3. The filter of claim 1 wherein the expanded chamber comprises wherein the inner wall is microporous.

4. The filter of claim 1 wherein in use, the efficiency of the bubble-removing process is not dependent upon the fluid flow rate under stable flow conditions, and wherein the device works to remove air bubbles under a range of orientations.

5. The filter of claim 3 wherein the microporous membrane is comprised of a material selected from the group consisting of polytetrafluoroethylene, a glass composite, nylon, polyethersulfone, acrylic copolymer, vinylidene fluoride (VDF), tetrafluoroethylene, vinylidene fluoride, hexafluoropropylene, carbon black, and sulfur.

6. The filter of claim 3 wherein the microporous membrane becomes increasingly gas permeable with increasing liquid pressures within the liquid flow path.

7. The filter of claim 6 wherein, in use, the pores tend to close under conditions of negative gauge pressure, inhibiting gas flow into the filter, but tend to open under conditions of positive gauge pressure, allowing gas flow out of the filter.

8. The filter of claim 3 wherein the microporous membrane comprises pores that are diamond shaped.

9. The filter of claim 3 wherein the outer wall comprises a perforated, gas permeable material.

10. The filter of claim 3 wherein the outer wall comprises a material that is impermeable to gas and has valves integrated within it.

11. The filter of claim 3 wherein, in use, the filter acts passively and automatically to trap and air bubbles present in the liquid flowing through the line.

12. The filter of claim 3 wherein, in use, gas bubbles are captured and vented while concurrently using instruments passing through the liquid carrying line.

13. The filter of claim 3 wherein, in use, with fluids having an inertia of up to Re=4800, filtration efficacy is independent of flow rate.

14. The filter of claim 3 wherein, in use, accumulated gas bubbles present in a liquid-carrying line are removed regardless of the orientation of the filter.

15. The filter of claim 3 wherein the filter is adapted to be inserted in-line into a conduit to provide a single-channel through which liquid passes and gases are captured and vented.

16. A system comprising the filter of claim 1 and a conduit, where the filter is placed in-line with the conduit.

17. The system of claim 16 wherein the conduit is part of a device selected from the group consisting of an intravenous line, an arterial line, a catheter, a sheath, a microfluidic device, a liquid chromatography device, a spectrophotometer, a nucleotide sequencer, an analytical device, and an ink-jet printing device.

18. The system of claim 16 wherein, in use, gases are captured and vented while concurrently using instruments passing through the liquid carrying line.

19. The system of claim 16 specifically employing a single channel design, and not a split channel design.

* * * * *